(12) United States Patent
Singh

(10) Patent No.: US 9,064,243 B2
(45) Date of Patent: Jun. 23, 2015

(54) SYSTEM AND METHOD FOR COMMUNICATING PRESENCE STATUS

(75) Inventor: Jasjit Singh, Redwood City, CA (US)

(73) Assignee: BlackBerry Limited, Waterloo, Ontario (CA)

( * ) Notice: Subject to any disclaimer, the term of this patent is extended or adjusted under 35 U.S.C. 154(b) by 175 days.

(21) Appl. No.: 13/398,430

(22) Filed: Feb. 16, 2012

(65) Prior Publication Data

US 2013/0217350 A1    Aug. 22, 2013

(51) Int. Cl.

| G06F 3/033 | (2013.01) |
|---|---|
| G06Q 10/10 | (2012.01) |
| G06Q 50/00 | (2012.01) |
| H04B 1/06 | (2006.01) |
| H04L 12/58 | (2006.01) |
| G06F 19/00 | (2011.01) |

(52) U.S. Cl.
CPC .......... *G06Q 10/107* (2013.01); *G06F 19/3418* (2013.01); *G06Q 10/109* (2013.01); *G06Q 50/01* (2013.01); *H04B 1/06* (2013.01); *H04L 51/043* (2013.01)

(58) Field of Classification Search
CPC ...... A61B 5/0402; A61B 7/04; A61B 5/0488; A61B 5/0006; A61B 5/0476; A61B 5/6816; A61B 5/04005; A61B 5/14532; A61B 5/4806; A61B 5/742; A61B 5/0452; A61B 5/224; A61B 8/488; G06F 19/3418; G06F 19/345; G01C 15/04; H04B 1/06
USPC .............. 455/130; 702/19, 188; 715/841, 757
See application file for complete search history.

(56) References Cited

U.S. PATENT DOCUMENTS

| 7,921,369 | B2 * | 4/2011 | Bill ............................... 715/753 |
| 8,171,076 | B2 * | 5/2012 | Matsunaga .................... 709/203 |
| 8,285,257 | B2 * | 10/2012 | Isobe et al. ................ 455/412.2 |
| 8,443,290 | B2 * | 5/2013 | Bill ............................... 715/753 |
| 2008/0184170 | A1 * | 7/2008 | Periyalwar .................... 715/841 |
| 2008/0242231 | A1 | 10/2008 | Gray |
| 2009/0170480 | A1 * | 7/2009 | Lee ........................... 455/414.1 |
| 2009/0300525 | A1 * | 12/2009 | Jolliff et al. .................. 715/764 |
| 2010/0250325 | A1 | 9/2010 | Pradeep et al. |
| 2011/0040155 | A1 * | 2/2011 | Guzak et al. .................. 600/300 |
| 2012/0095979 | A1 * | 4/2012 | Aftab et al. ................... 707/706 |
| 2012/0142318 | A1 * | 6/2012 | Okon ............................ 455/413 |
| 2013/0167052 | A1 * | 6/2013 | Niesslein et al. ............. 715/764 |
| 2013/0196633 | A1 * | 8/2013 | Wesby van-Swaay ........ 455/411 |
| 2013/0217350 | A1 * | 8/2013 | Singh ............................ 455/130 |

OTHER PUBLICATIONS

El Barachi, M. et al.; "The Design and Implementation of Architectural Components for the Integration of the IP Multimedia Subsystem and Wireless Sensor Networks"; Topics in Design & Implementation; IEEE Communication Magazine; Apr. 2010; pp. 42 to 50; vol. 48, No. 4; IEEE Service Center; Piscataway, U.S.A.; ISSN: 0163-6804.

(Continued)

*Primary Examiner* — Fayyaz Alam
*Assistant Examiner* — Max Mathew
(74) *Attorney, Agent, or Firm* — Fleit Gibbons Gutman Bongini & Bianco P.L.

(57) ABSTRACT

A method and system are provided for computing a physiological presence of a user of a device. The method comprises obtaining a physiological measurement of the user of the device and computing a presence status based on physiological measurements.

18 Claims, 13 Drawing Sheets

(56) References Cited

OTHER PUBLICATIONS

Aimejrad, A.S.; "Human Emotions Detection using Brain Wave Signals: A Challenging"; European Journal of Scientific Research; 2010; pp. 640 to 659; vol. 44, No. 4; EuroJournals Publishing, Inc; ISSN: 1450-216X; http://www.eurojournals.com/ejsr_44_4_14.pdf.

Campbell, A.T. et al.; "NeuroPhone: Brain-Mobile Phone Interface using a Wireless EEG Headset"; Proceedings of the second ACM SIGCOMM workshop on Networking, systems, and applications on mobile handhelds (MobiHeld 2010); New Delhi, India; Aug. 30, 2010; pp. 3 to 8; ACM; ISBN: 978-1-4503-0197-8; http://www.cs.dartmouth.edu/~campbell/papers/neurophone.pdf.

Yazdani, A. et al.; "Implicit Emotional Tagging of Multimedia Using EEG Signals and Brain Computer Interface"; Proceedings of the first SIGMM workshop on Social media (WSM '09); Beijing, China; Oct. 23, 2009; p. 81 to 88; ACM; ISBN: 978-1-60558-759-2.

Dennis, K.; "Opening Pandora's Box: How technologies of communication and cognition may be shifting towards a 'Psycho-Civilized Society'"; First Monday [Online]; Feb. 25, 2008; vol. 13, No. 2.

Carr, N.; "New frontiers in social networking"; Rough Type: Nicholas Carr's Blog—New frontiers in social networking; Aug. 2010; http://www.roughtype.com/archives/2010/08/new_frontiers_i_1.php; retrieved Jun. 6, 2011.

"PLX Unveils the XWave, Brainwave Interface for Apple Products"; Aug. 16, 2010; PLX Devices Inc.

Ford, J.; "XWave iPhone Accessory Channels Your Brain Waves into iPhone"; RTR.org Social Network—iPhone Accessory from XWave . . .; Jan. 7, 2011; http://www.rtr.org/blogs/5252/8186/i-phone-accessory-from-xwave-chan; retrieved Jun. 7, 2011.

PLX XWave—Brainwave to iPhone Interface; Online at least as early as Jun. 7, 2011; PLX Devices Inc.; http://www.plxwave.com/apps/xwavetunes/index.html; retrieved Jun. 7, 2011.

Biexpression idea; Emotiv Forum; Jan. 22, 2011; http://www.emotiv.com/forum/forum4/topic1175; retrieved Jun. 8, 2011.

EmoLens; Emotiv Application Store; Online at least as early as Jun. 8, 2011; http://www.emotiv.com/store/apps/applications/118/3886; retrieved Jun. 8, 2011.

Boyle, R.; "EEG Monitoring Headband Could Index Movies by Emotion"; Online at least as early as Jun. 8, 2011; http://gizmodo.com/5623892/eeg-monitoring-headband-could-index-movies-by-emotion; retrieved Jun. 8, 2011.

Aamoth, D.; "XWave iPhone Headset Promises to Read your Mind"; XWave iPhone Headset Promises to Read Your Mind—Techland—Time.com; Nov. 26, 2010; pp. 1 to 5; http://techland.time.com/2010/11/26/xwave-iphone-headset-promises-to-read-your-mind/; retrieved Jun. 7, 2011.

Schwartz, P. et al; "Quantum Leap Brain prosthetics. Telepathy. Punctual flights. A futurist's vision of where quantum computers will take us"; Aug. 2, 2006 CNNMoney [Online]; http://money.cnn.com/2006/07/26/magazines/fortune/futureoftech_quantum.fortune/index.htm; retrieved Jun. 7, 2011.

Biro, U. B.; Search Report from corresponding European Application No. 12155842.3; search completed Jul. 4, 2012.

* cited by examiner

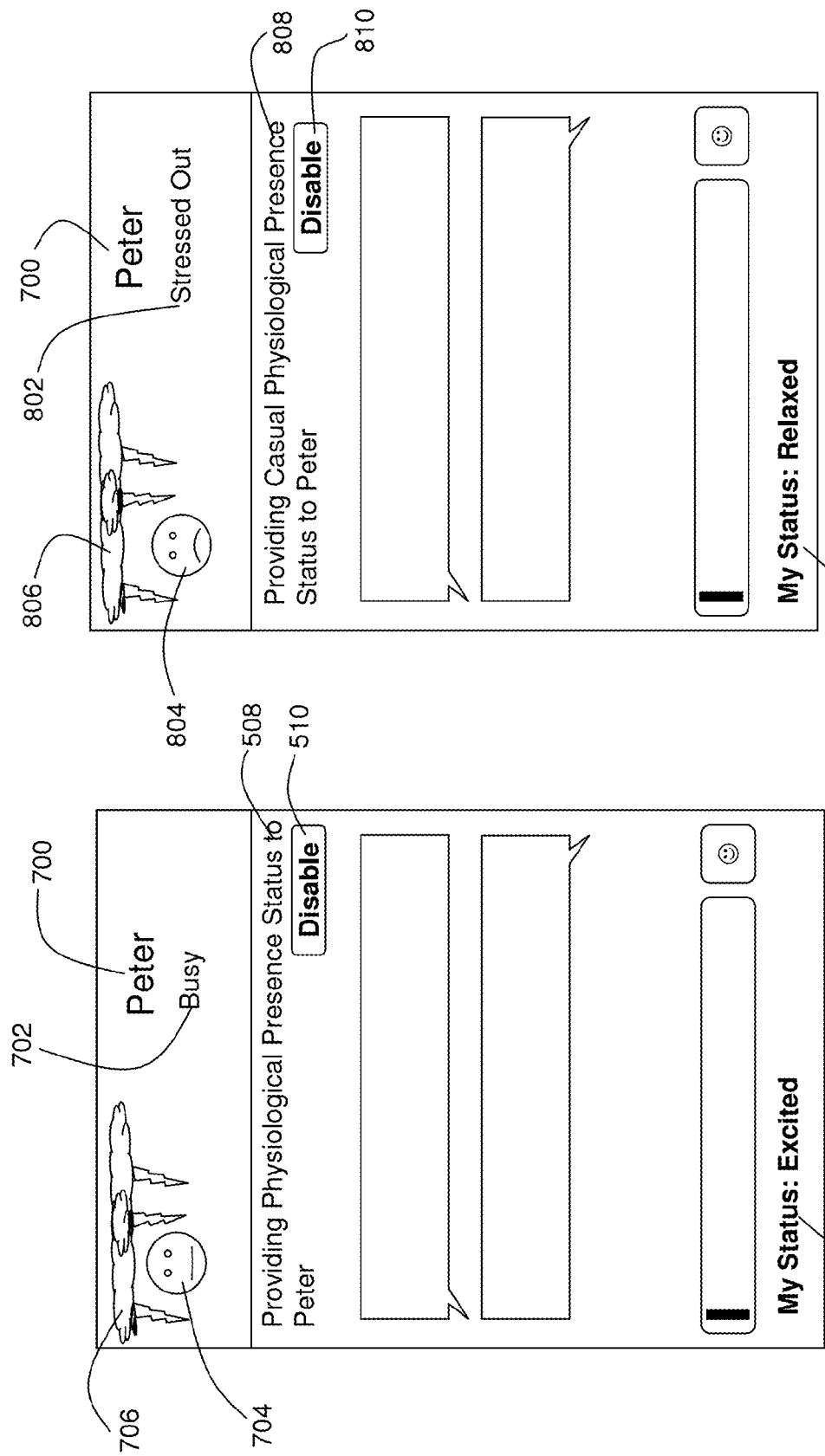

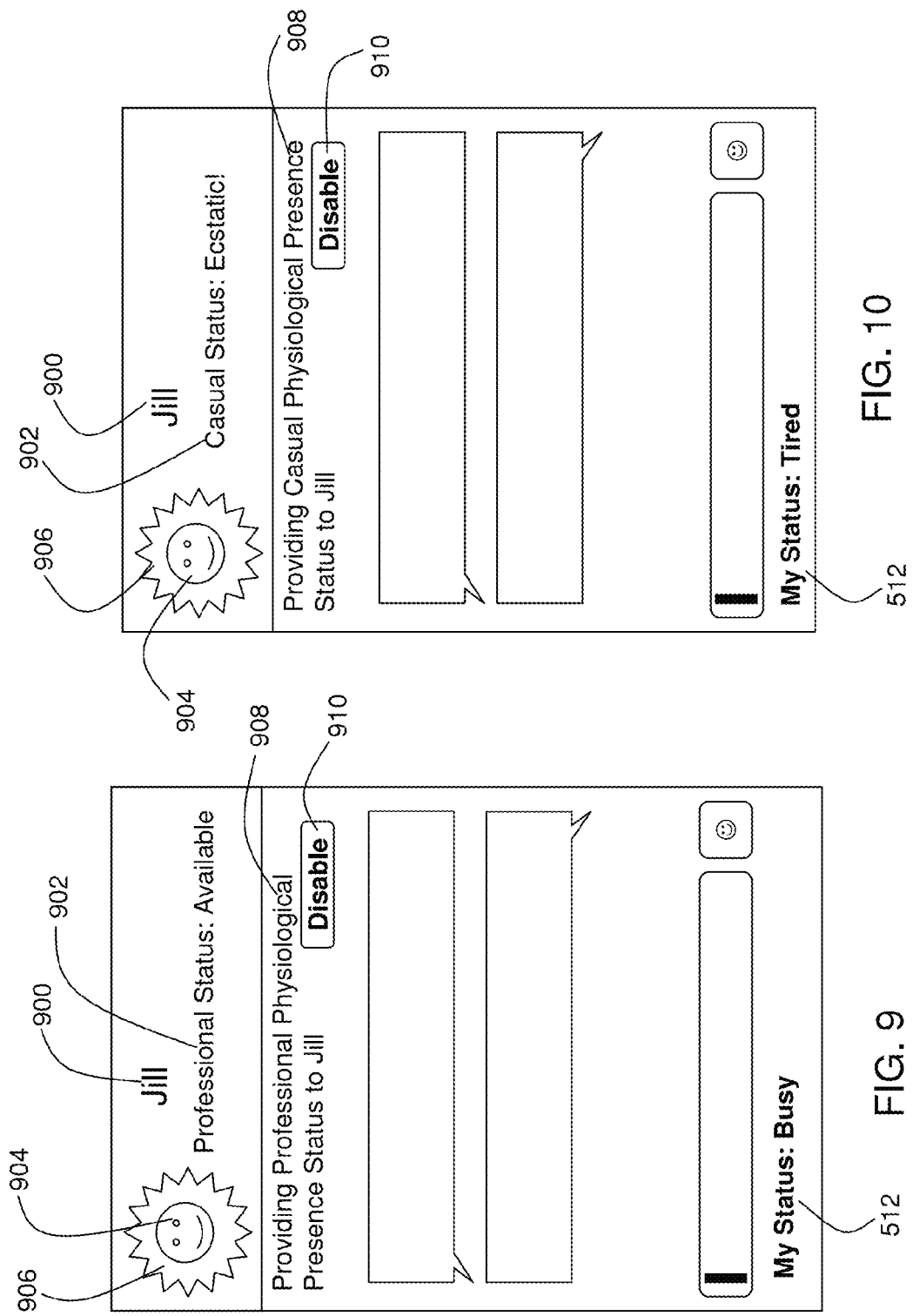

SYSTEM AND METHOD FOR COMMUNICATING PRESENCE STATUS

TECHNICAL FIELD

The following relates to systems and method for communicating presence status.

DESCRIPTION OF THE RELATED ART

Mobile communication devices can be used to exchange messages and/or data. For example, data and messages can be exchanged between devices via email, instant messaging (IM), a short messaging service (SMS), file transfers using short and long range communication protocols, etc. Mobile communication devices are often also configured to provide cellular telephony services, voice communications over an internet connection (e.g., via Wi-Fi), or both.

Messages exchanged between devices typically include text and may include one or more attachments, including data files, video files, audio files, etc. Messages may be used for personal or professional communication.

Messaging applications often allow a user to specify a presence status. A presence status typically indicates whether a user of a messaging application is available or unavailable for communication. A user typically enters or selects a status from a list of possible options. The presence status may also be derived based on the user's interactions with an electronic device.

BRIEF DESCRIPTION OF THE DRAWINGS

Embodiments will now be described by way of example only with reference to the appended drawings wherein:

FIG. 7 is an example screenshot of an instant messaging screen showing physiological presence status being shared with a remote mobile device;

FIG. 8 is an example screenshot of an instant messaging screen showing casual physiological presence status being shared with a remote mobile device;

FIG. 9 is an example screenshot of an instant messaging screen showing professional physiological presence status being shared with a remote mobile device;

FIG. 10 is an example screenshot of an instant messaging screen showing casual physiological presence status being shared with a remote mobile device;

DETAILED DESCRIPTION

Figure 1:
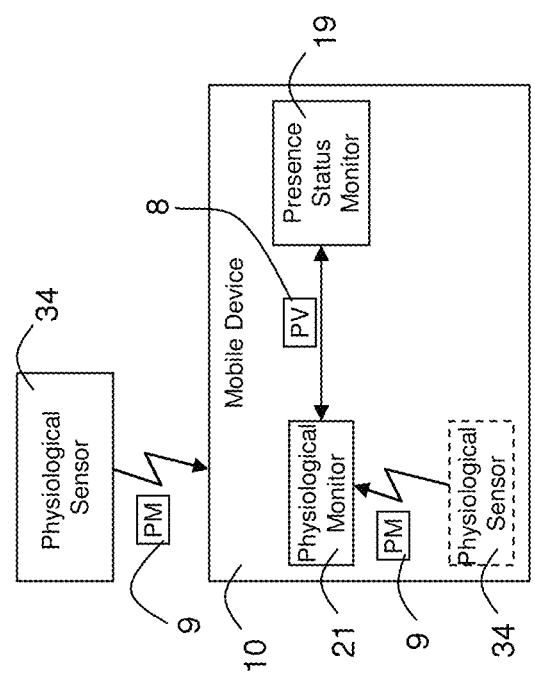
FIG. 1 is a block diagram of an example of a mobile device.

It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

A system and method for computing and sharing physiological presence status information with remote devices are provided. The system enables physiological presence status to be shared according to settings associated with the user of a remote device.

Communications that are facilitated via a messaging service and application, such as IM, can utilize presence status settings to control the manner in which such communications are handled. For example, a status option can be provided to block communications when that status option has been selected. One or more status options may also cause the communications to be diverted, presented with associated content, or cause a setting on the recipient device to be otherwise modified.

An accurate and up-to-date presence status is useful to users of communication devices. Because presence status signals the user's ability or interest to communicate at a certain point in time, an incorrect or old presence status can cause the user to receive unwanted communications. An incorrect presence status may also prevent the user from receiving welcome communications. For example, if the presence status of a user of a first mobile device is set to "busy", the user of a second mobile device may know not to disrupt the user of a first mobile device. If the user of the second device is not busy despite having such a status, the user may not receive welcome communication. Alternatively, if the user of the first device is a subordinate of the user of the second device, an inaccurate presence status for the subordinate user of "available" may indicate to the supervisor that the subordinate does has capacity to take on additional work. The supervisor may then distribute additional work to the user with the "available" presence status, despite that user being busy.

A presence status of "busy" may also instruct applications on the mobile device to behave differently than if the user's presence status was set to "available". For example, the messaging application may notify users with an "available" presence status of each incoming message. Conversely, the messaging application may not notify users with a "busy" presence status of each incoming message.

It has been recognized that an accurate presence status can also enable a user of a first communication device to gauge the emotional state of a user of a second communication device with whom the first user is communicating. Awareness of the emotional state of a communication partner can enable the user to communicate in an appropriate context. For example, if a first user of a first mobile device is upset, a second user of a second mobile device in communication with the first mobile device may acknowledge the first user's emotional state, which may facilitate communication between the two parties. In this way, based on the emotional state of the first user, the second user of the second mobile device may also refrain from bringing up certain topics in conversation that may upset the first user.

The presence status option may be manually selected. For example, the user manually selects a new presence status from a list when the user wishes to make others aware of a changed presence status. Alternatively, presence status may be derived from the user's activities on the device. For example, the user's presence status may be set to "Away" if the user has not interacted with the device for a predetermined period of time.

Manual input of a presence status can require that the user interrupt other activities with the device to adjust the presence. Because in such cases the user interrupts other activities to adjust the presence status, the user may not update the presence status file as frequently as the user may wish the presence status to be updated. The user's presence status may also be changing too frequently to make timely manual adjustments to the presence status.

Moreover, since viewers of the user's presence status are aware that the user has manually selected a particular presence, the user may be hesitant to set the presence status to certain settings, for example, emotional settings. The user may also be unaware of a presence status that would properly describe the user's physiological or emotional status. For example, the user may not be aware of an increasing heart rate or an increasing tiredness.

Setting the presence status based on an interaction with the device only captures a limited spectrum of the user's true availability. For example, the device will not know whether a user who has not updated the device for a predetermined period of time is sleeping or exercising. In particular, presence statuses that are unassociated with direct interactions with the device are unknowable. For example, setting the presence status based on interactions with the device may not be able to capture the user's level of excitement or the user's mood.

Furthermore, providing only a single presence status that is shared with all contacts does not allow a user to limit certain contacts to receiving only certain types of presence settings. For example, the user may wish to have one type of presence status viewable by friends and another type of presence status viewable by work colleagues. The user may also wish to have one presence status as a manually adjusted presence status and a separate physiological presence status for sharing physiological presence.

For example, the user may wish to limit the type of presence status that colleagues can view to status updates related to their work activities such as "busy", "available", "out of the office", "on vacation", "overworked", etc. A user may wish that friends are able to view more casual presence settings, for example, "happy", "excited", "angry", "confused", etc. Limiting the types of presence status shared with certain groups enables the user to express all types of availability including emotions to friends without compromising their behavior towards professional colleagues.

A first user in communication with a second user may elect to share only a "professional" physiological presence status whereas the second user may wish to provide a "casual" physiological presence status to the first user. A user may also wish to provide casual physiological presence status to all known contacts, however, use a more restricted, professional physiological presence status when publishing online or sharing with a larger group of recipients. A user may also wish to temporarily restrict the range of emotions being provided by the physiological presence status.

Although the examples described herein refer to professional and casual physiological presence status, it will be appreciated that other categories of physiological presence status may also be used.

It can be appreciated that "presence status" as discussed herein may refer to any status indicator that conveys the ability, and/or willingness, and/or a physiological state of a potential communication partner, e.g., a user, to communicate. In particular, the presence status may comprise the physiological state of a user or the physiological state of the user may be provided separately to the presence status and referred to as a physiological presence status. As such, both the presence status and the physiological presence status, as defined herein, may comprise physiological presence status. The presence status may also be determined based on physiological presence status as well as presence status determined using other methods.

The physiological presence status may comprise any status derived from physiological measurements of a user of a device including, but not limited to, an electroencephalography sensor, a thermometer, a heart rate monitor, a blood pressure monitor, a magnetic resonance imaging device, etc. The physiological presence status may comprise emotional status, the level of excitation, stress levels, health, and other indicators that can be derived from physiological measurements of a subject.

The physiological state of a user of a communication device may be captured by a sensor in communication with the user. The sensor may comprise an electroencephalography (EEG) sensor, a heart rate monitor, an accelerometer, a thermometer, etc. The sensor may be comprised of a combination of sensors. For example, the sensor may comprise an EEG sensor and a heart rate monitor. The sensor performs a physiological measurement and provides the physiological measurement to the mobile device, which may store the physiological measurement in a database. A physiological monitor in the mobile device may also generate presence values based on the physiological measurements and store these values in the database, as is further described herein.

The physiological presence file may be used in various applications on a communications device, for example, in instant messaging applications or in calendar applications. The physiological presence status may be combined with another type of presence status, for example, manually selected presence. The physiological presence status may be used in real time. Historical physiological presence status may also be stored. Real time physiological presence status may be compared with historical presence status to determine relationships between current data and historical data.

User configurable settings on the mobile communication device may enable a user to restrict which physiological presence statuses are shared with other devices. User configurable settings on the mobile device may also enable a user to share particular types of physiological presence status. User configurable options may enable a user of a device to share physiological presence status for only a predetermined period of time.

Although examples related to using physiological presence status to set an instant messaging presence status are provided, it is to be understood that the physiological presence status can be used with a number of applications. These applications may include a calendar, content streaming service (e.g., news, music streaming, video streaming), e-mail, video communication applications, navigation application, etc.

The physiological presence status may also be used with individual elements of an application. For example, an instant messaging application may tag each message with the user's physiological presence status at the time that the message is sent. A calendar application may also tag calendar appointments with physiological presence status to provide all those who can view the appointment with an indication of what the user's presence status was at the time that the appointment was created or at any time thereafter. An application that shares photographs may allow a physiological presence status to be appended to each photograph.

Similarly, a user's presence status in a music sharing application may tag each song that the user has listened to with the user's physiological presence status. Other users with a similar presence status may be provided with a recommendation to listen to the song. The mobile device or a content streaming server may be configured to recommend that the user share the song with friends who currently have, or historically have had, a similar presence status. The physiological presence status in any of the examples may be a professional physiological presence status, a casual physiological presence status or any other user-configurable category for physiological presence status.

Presence statuses generated based on physiological measurements may reduce the likelihood that a user selects an inaccurate presence status or uses an outdated presence status. Since the physiological presence status requires no explicit action from the user, a physiological presence status may not be erroneously selected by the user. However, the mobile device may be provided with an option to override the physiological presence status in favor of another type of presence status, for example, a manually selected presence status. An override option enables the user to prevent physiological presence status from being shared and enables a user to use another type of presence status.

It has been realized that when a user's ability to make a change to the presence status is hindered by an activity, lack of awareness of an appropriate presence status, or a lack of desire to manually update the presence status, an improved method of setting the user's presence status is needed.

In the following, methods and systems are provided to set the presence status of a user based on one or more physiological signals. In particular, methods and systems are provided to set the physiological presence status of a device user and to share the physiological presence status with other devices over a network. Methods and systems to restrict which physiological presence statuses are shared are also provided.

It will be appreciated that although the following examples are provided in the context of a mobile device, the principles discussed herein are equally applicable to other communication devices, for example, personal computers, laptops, tablet computers, telephones, medical devices (e.g., hearing aids), communication systems in vehicles, etc.

The mobile device can be a two-way communication device with advanced data communication capabilities including the capability to communicate with other mobile devices 10 (see FIG. 1) or computer systems through a network of transceiver stations. The mobile device 10 may also be a server, for example, a content streaming server. The mobile device 10 may also have the capability to allow voice communications. Depending on the functionality provided by the mobile device, the mobile device may be referred to as a data messaging device, a two-way pager, a cellular telephone with data messaging capabilities, a wireless Internet appliance, or a data communication device (with or without telephony capabilities). The mobile device can also be one that is used in a system that is configured for continuously routing all forms of pushed information from a host system to the mobile device. The following examples include communications between mobile or handheld devices, which will be referred to collectively as mobile devices and be referred to by numeral 10.

FIG. 1 is a block diagram of an example mobile device 10. The mobile device 10 may be in communication with a physiological sensor 34, which may be located outside of the mobile device 10 or may be an integrated component of the mobile device 10. The mobile device 10 comprises a physiological monitor 21, which is operable to obtain physiological measurements 9 from a physiological sensor 34. The mobile device 10 further comprises a presence status monitor 19, which is operable to receive physiological values 8 from the physiological monitor 21. The presence status monitor 19 may also obtain information from other modules (not shown) that may be present on the mobile device 10.

The mobile device 10 also comprises a memory and a processor which are in communication with the physiological monitor 21 and the presence status monitor 19. The memory may have stored thereon computer instructions which, when executed by the processor, provide the functionality as described herein. A memory and processor in communication with the mobile device 10 may also be located remotely, for example, in "the cloud".

The physiological sensor 34 acquires physiological measurements 9 (PM as shown in the figures) for the physiological monitor 21 on the mobile device 10. The physiological monitor 21 calculates a presence value 8 (PV as shown in the figures) and provides the presence value 8 to the presence status monitor 19. Once the presence status monitor obtains the presence value 8, the presence status monitor 19 may calculate a user's presence. The presence status monitor 19 may also provide the user's presence information to other mobile devices 10, a server, or the presence status monitor 19 may store the user's presence information.

The presence status monitor 19 is operable to generate and control the presence status of a user of the mobile device 10. The presence status monitor 19 may generate the user's physiological presence status based on information received from the physiological monitor 21. The presence status monitor 19 may also store the presence status and share the presence status with any other applications and modules located on, or in communication with, the mobile device 10. The presence status monitor 19 is also operable to share the user's presence status with other devices over a network 200 (see FIG. 2). The presence status monitor 19 may be operable to store presence information in a presence status to enable calculation of historical presence information and generate the instantaneous physiological presence status in relation to typical physiological values for a particular user of a mobile device 10.

The presence status monitor 19 may be operable to determine whether the physiological data obtained by the physiological sensor 34 is out of the range of normal physiological values for a particular user of a mobile device 10. For example, if the physiological sensor 34 comprises an EEG sensor, the presence status monitor 19 may be operable to generate a range of EEG values typical to the user of the mobile device 10 and store these values. The presence status monitor 19 may update the user's presence status when the values provided by the EEG sensor on the physiological sensor 34 are outside of the range of typical or historical EEG values for that user.

Other applications, for example, a messaging application, may be operable to store and share a separate physiological presence status based on information acquired by the physiological sensor 34. For example, the user may download an application that is operable to generate the user's presence status based on measurements received from the physiological sensor 34 using different computation steps than those used by the presence status monitor 19.

Figure 2:
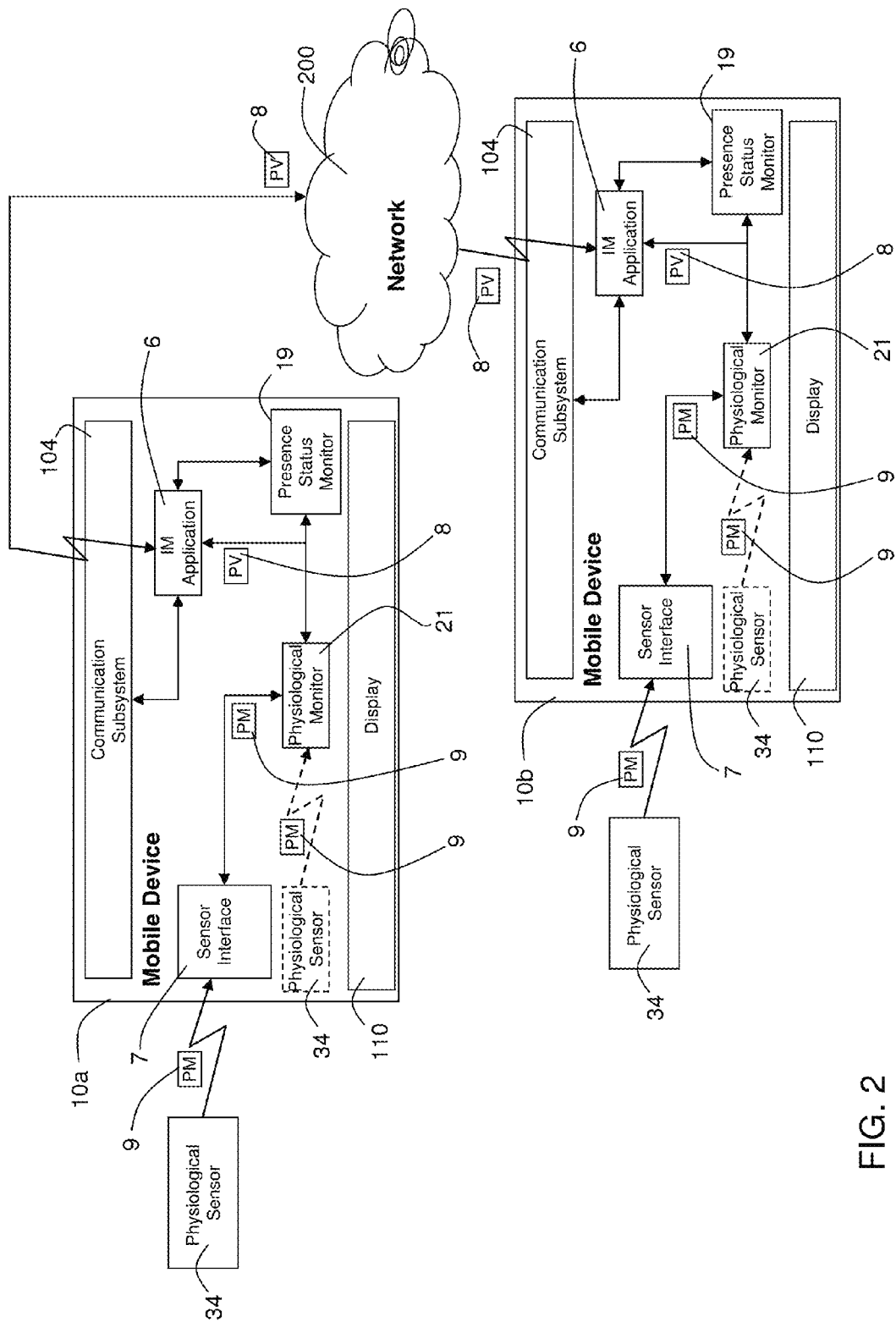
FIG. 2 is a block diagram of an example first mobile device in communication with an example second mobile device over a network.

Turning now to FIG. 2, a pair of mobile devices 10a, 10b are shown in communication over a network 200. The mobile devices 10a, 10b each comprise a physiological monitor 21, which is in communication with a physiological sensor 34 and a presence status monitor 19. If the physiological monitor 21 is in communication with an external physiological sensor 34, the mobile device 10a, 10b may further be provided with a sensor interface 7 through which physiological measurements may be transferred into the mobile device 10. Each mobile device 10a, 10b may further comprise a communication subsystem 104 used to communicate with the communication subsystem 104 of another device through a network 200. The communication subsystem 104 may be operable to share presence values via the network 200. Each of the mobile devices 10a, 10b further comprises one or more applications. The mobile devices 10a, 10b may comprise, for example, an instant messaging application 6, which is operable to make use of a presence value to inform the user of a remote device 10a of the presence of the user of the local device 10b.

Each of the mobile devices 10a, 10b in the example shown comprises a display 110 which is configured to display physiological presence status of either the user of the local mobile device 10a or the user of the remote device 10b. Although the mobile devices 10a, 10b are shown with only a display 110, it is to be understood that the mobile devices 10a, 10b may also comprise various other input and output devices such as a keyboard, speakers, microphone, a camera, various sensors, etc. As such, it can be appreciated that the configuration shown in FIG. 2 is for illustrative purposes only.

The physiological sensor 34 provides a physiological measurement 9 to the physiological monitor 21 of the mobile device 10 via the sensor interface 7. The physiological monitor 21, as is described above, may also obtain one or more physiological measurements 9 from an onboard physiological sensor 34. The physiological monitor 21, upon obtaining a physiological measurement 9, is operable to calculate a presence value 8 to provide to the instant messaging application 6 and the presence status monitor 19. The instant messaging application 6 may be operable to share a user's physiological status with an instant messaging application 6 on a remote mobile device 10 over the network 200.

Figure 4:
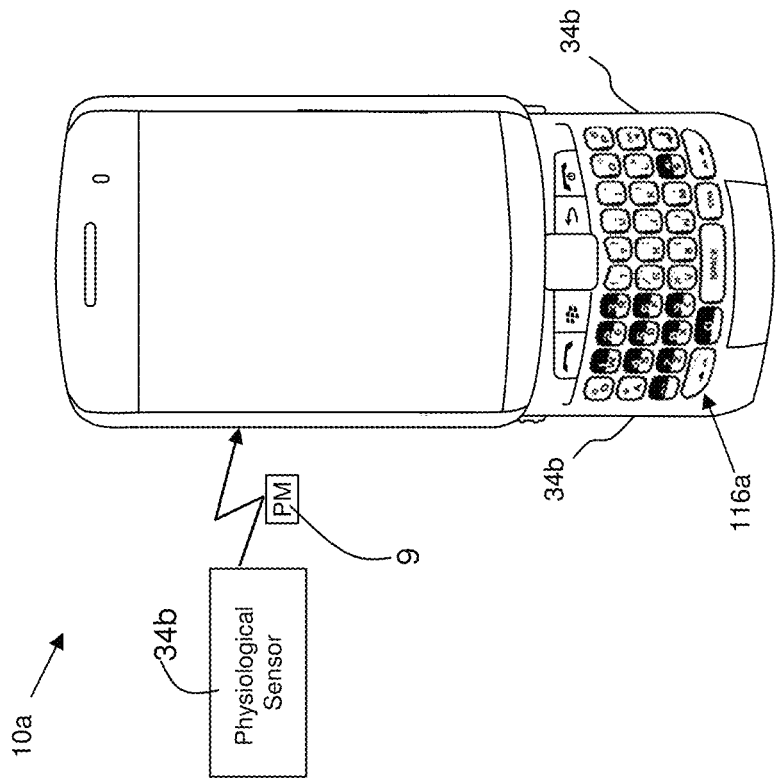
FIG. 4 is a diagram of an example mobile device in communication with a physiological sensor.
Figure 3:
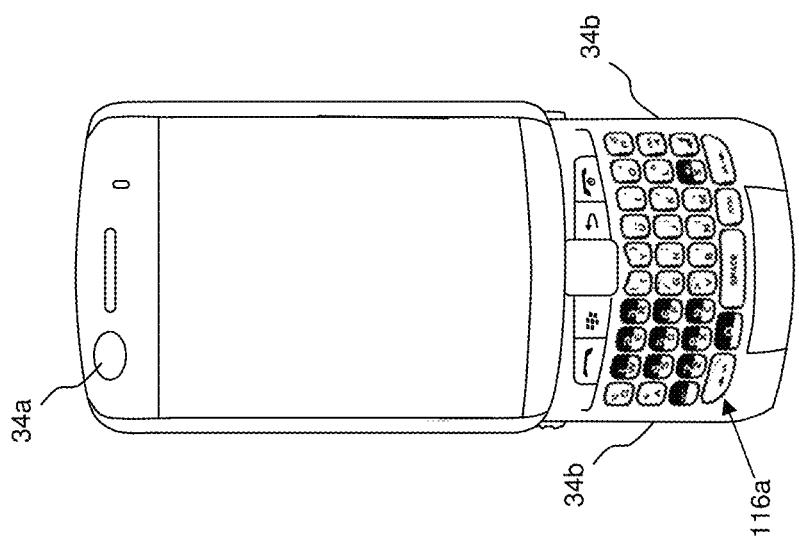
FIG. 3. is a diagram of an example mobile device comprising an onboard physiological sensor.

FIG. 3 shows an external view of the mobile device 10 of FIG. 1 in communication with a physiological sensor 34a integrated in the mobile device 10. The mobile device 10 may comprise an internal physiological sensor 34a, as is shown in FIG. 3, or the mobile device 10 may comprise an external physiological sensor 34b, as is shown in FIG. 4. If housed external to the mobile device 10, the physiological sensor 34 may be a stand-alone external sensor. The physiological sensor 34 may be housed with a set of earphones or a communication headset, which is worn by the user and typically includes a microphone and a speaker. A headset is often worn in order to avoid having to hold the mobile device 10 adjacent to the user's ear. The advantage of embedding a physiological sensor 34 in a headset is that the user may be wearing the headset while manipulating the mobile device 10 or while the mobile device is stored away from the user's body or in the user's pocket. The user's presence status may be updated continuously or at predetermined intervals while the user is wearing the headset. Moreover, a headset is worn on the user's head, which enables a physiological sensor 34 comprising an EEG sensor to collect EEG signals. The physiological sensor 34 may be in communication with the mobile device 10 through a cabled connection or a wireless connection.

Referring again to FIG. 3, an example mobile device 10a comprises an integrated physiological sensor 34a. The physiological sensor 34a is located near the speaker, which is typically in contact or in proximity to the user's ear during a telephone conversation. A second physiological sensor 34b may also be provided on the back side or the sides of the mobile device to collect physiological data while the user is manipulating the device 10a. For example, if the user is using the keyboard 116a to communicate using the instant messaging application 6, the user's hands may grip the physiological sensors 34b on the back and sides of the mobile device 10a, allowing the physiological sensors 34 to capture physiological information from the user's hands, for example, the user's heart rate. The mobile device 10 may comprise an external physiological sensor 34 in addition to the one or more physiological sensors 34 housed in the device.

Various software applications and components may be stored on and used with the mobile device 10. For example, calendar application, instant message application, phone application, address book and a profiles application may be provided on the mobile device 10. These applications can access information stored on the mobile device, e.g., appointments, host buddy list, ringtones, contacts, etc. The contacts stored in the contact database include address information, instant messaging information, group information, and presence status sharing information. For example, an entry in contact database may comprise information detailing what type of presence status is shared with the entry.

The user of the mobile device 10 may elect to share presence status information with the entry in the contact database but decline to share physiological presence status, or any other presence status derived from measurements by the physiological sensor 34. Group information may comprise a list of contacts in each group and information detailing what type of presence status is shared with the group. For example, the user of the mobile device 10 may elect to share only certain types of information derived from measurements made by the physiological sensor with a particular group.

It will be appreciated that the various applications may operate independently or may utilize features of other applications. For example, the phone application and instant messaging application 6 may use the address book for contact details obtained from a list of contacts. The instant messaging application 6 may store contacts or groups of contacts in a buddy list. The buddy list may also store information relating to which presence status is shared with each contact or group of contacts.

Figures 5, 6:
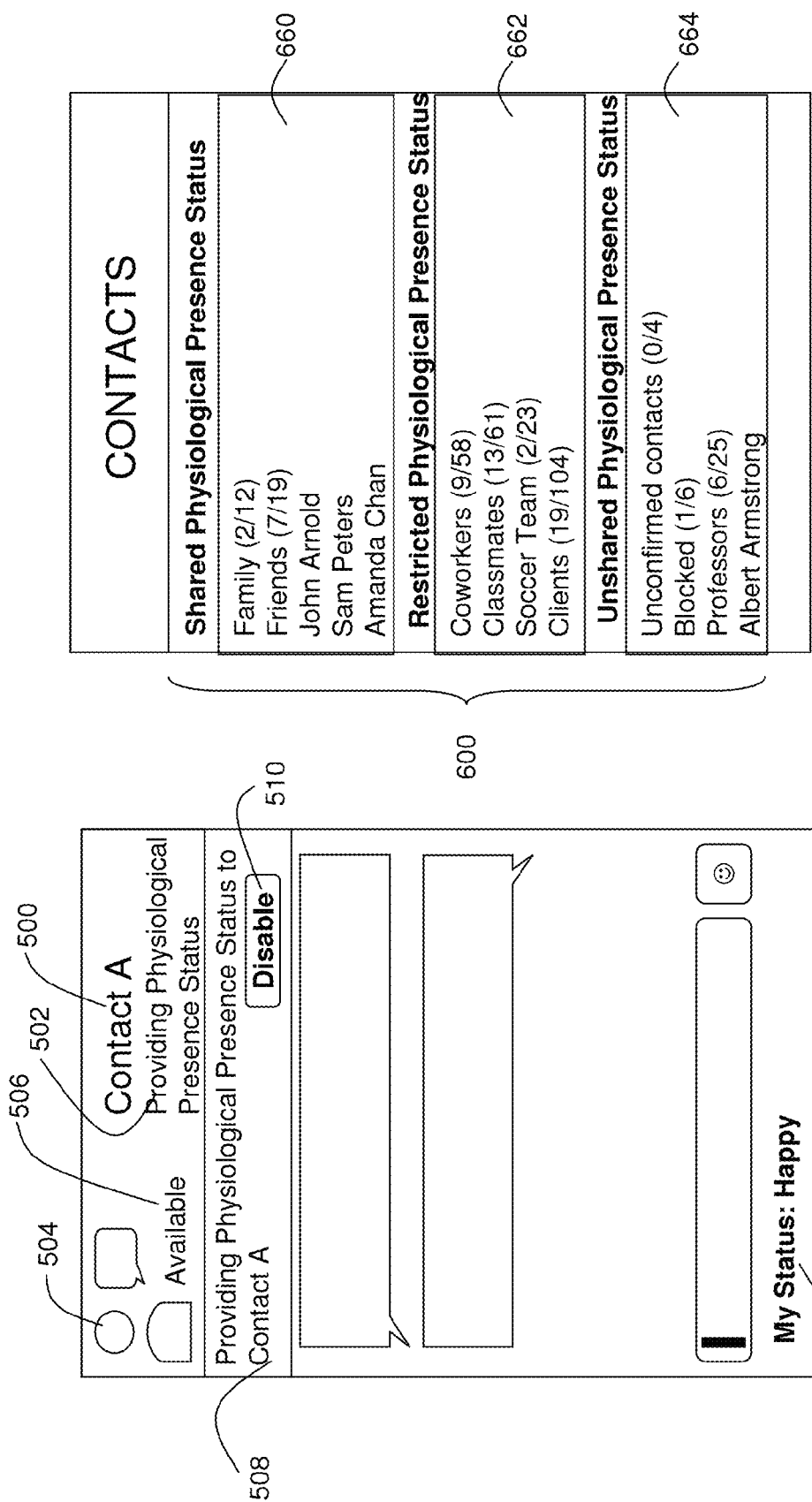
FIG. 5 is a screenshot of an example instant messaging screen wherein physiological presence status is being shared with a remote mobile device.
FIG. 6 is an example screenshot of a list of instant messaging contacts organized by groups.

Referring now to FIG. 5, a screenshot of a messaging screen of an instant messaging application 6 is shown. A user of the mobile device 10 may be able to view the contact 500 with whom the user is communicating, which, in the example shown is "Contact A". The screen may also display whether or not Contact A is providing physiological presence status 502. An avatar 504 or other representation of the user may also be displayed as well as the physiological presence status provided by that user 506. The user of the mobile device 10 may also be provided with an indication 508 that informs the user whether the user's physiological presence status is being shared with Contact A. The user's physiological presence status may also be displayed using an indication 512 to enable the user to able to view the presence status that the user is providing to his/her conversation partners. An option 510 to disable the sharing of the user's physiological presence status may also be provided 510.

Turning to FIG. 6, a list of the contacts 600 of the user of the mobile device 10 is shown. The contacts may be organized by groups. For example, the groups may be divided into those with which the user shares physiological presence status 660, those with which the user shares a restricted physiological presence status 662 such as a professional physiological presence status and those with whom the user does not share physiological presence status 664. As is described above, a user may elect to provide physiological presence status to other users based on the other users'groups independently from the other users electing to provide physiological presence status.

Referring to FIG. 7, a screenshot similar to that of FIG. 5 is shown. The user of the mobile device 10 is in communication with a contact named "Peter", as is shown by the contact name 700. As can be seen from Peter's "Busy" status 702, Peter has elected to provide presence status to the user of the mobile device 10. Peter's presence status may comprise physiological presence status using indication 512. The physiological presence status may focus on a set of easily detectable emotions that may be helpful to share. For example, the emotions may correspond to those that a user may wish to show in the workplace. Peter's presence status may also comprise other factors used to determine Peter's availability and engagement in the conversation. Peter's presence status may be reinforced by an image, animation or other visual or auditory representation of Peter's status. In the example of FIG. 7, Peter's presence status is represented by an avatar with a serious face 704. Peter's presence status may also expressed by an analogical representation 706. In FIG. 7, Peter's presence status is represented by clouds and thunderbolts located above the emoticon. The clouds and thunderbolts indicate that Peter may not be in a good mood to be approached. For example, it may be advantageous to approach Peter with a request at a later time.

It may be advantageous to provide other parties in a conversation with a more complete interpretation of a user's physiological presence status. For example, it may be advantageous to provide friends with a textual, visual, audio, or other representation of the full range of emotions that the user may feel. Referring to FIG. 8, which is a screenshot similar to that of FIG. 7, an example illustrates the scenario wherein Peter is sharing a casual physiological presence status. Peter is "Stressed Out", according to Peter's textual presence status representation 802. The textual field 802 of physiological presence status may be updated in real time, at predetermined intervals, after certain events, or based on other factors. As can be seen by Peter's frowning avatar 804, Peter is likely in a bad mood. An analogical representation 806 is also shown alongside the avatar 804. The avatar 804, analogical representation 806, and textual representation 802 of the physiological presence status are provided only as examples of representations of presence status. The representation may also comprise a change in background color, a particular sound or song being played by the mobile device 10, the activation of an application or function of the mobile device 10, etc.

As can also be seen from FIG. 8, the user of the mobile device 10 is currently providing casual physiological presence status to Peter, as referred to by numeral 808. An option 810 to disable the sharing of casual physiological presence status information is also provided. An option to cease providing casual physiological presence status and providing professional physiological presence status instead may also be provided.

Turning to FIG. 9, a screenshot similar to FIG. 8 is shown. The user is conversing with a contact named "Jill" 900. The textual representation of Jill's presence status 902 in this example shows what status Jill is sharing as well as what her status is. In this case, Jill's professional presence status is "Available", indicating that she may be open to receiving requests. Providing the user with an indication as to whether Jill is sharing her full range of emotional statuses may be advantageous. Similarly to FIG. 8, a display showing that the user is providing professional physiological presence status 908 to Jill is shown, as well as an option to cease providing professional physiological presence status to Jill. Furthermore, an avatar 904 and an analogical representation of presence status 906 for Jill are also being shared.

Referring to FIG. 10, a screenshot of a user of a mobile device 10 who is communicating with Jill and sharing casual physiological presence status. In this case, Jill's status is "Ecstatic". A presence status such as "Ecstatic" may be advantageous to share with friends, however, Jill may wish to limit her professional presence status to protect her privacy, as she had done in the example of FIG. 9, to "Available".

The presence status monitor 19 may also be operable to set physiological presence statuses for more than three sharing categories. For example, the presence status monitor 19 may have a "professional" group, a "casual" group and a "family" group. The presence status monitor 19 may be operable to set physiological presence statuses for a user defined number of groups. The possible presence statuses for each category may also be user-defined or user-selectable.

Figure 11:
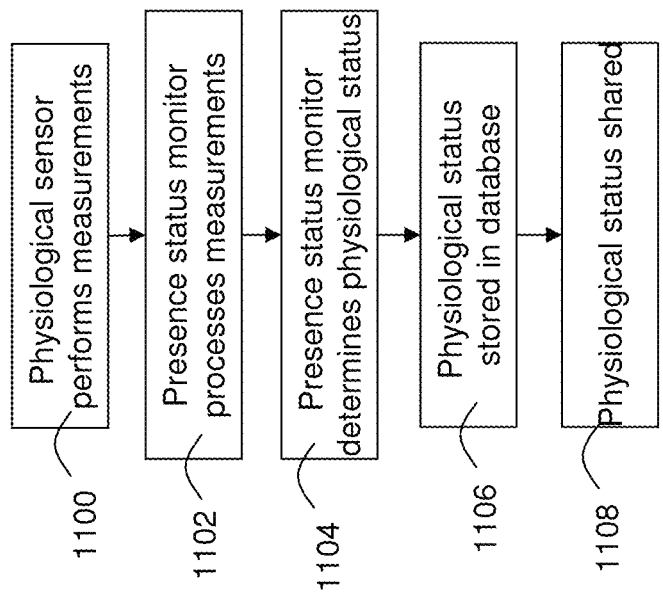
FIG. 11 is an process flow diagram of an example process for computing a physiological presence status.

Turning now to FIG. 11, an example flow diagram is provided illustrating computer executable operations that may be performed in creating a physiological presence status. The physiological sensor 34, as described above, may comprise several sensors including a heart rate monitor, thermometer, EEG, etc. The physiological sensor 34 performs a physiological measurement 9 of the user at 1100. At 1102, the presence status monitor 19 processes the physiological measurements 9 to provide physiological values 8 (e.g., the presence status monitor 19 may perform a statistical analysis on one or more physiological measurements 9 to produce one or more physiological values 8) that can be compared to control or historic physiological values 8. The physiological values 8 may also be compared with a particular group of individuals. At 1104, the presence status monitor 19 determines a physiological presence status, which may be incorporated with other factors into a presence status. The physiological presence status and/ or the presence status may be selected from a list of various presence statuses, each of which corresponds to a particular range of physiological values generated at 1102. At 1106, the presence status monitor 19 may be operable to store the presence status and/or physiological presence status in, for example, a presence status database included in or available to the presence status monitor 19. At 1108, the presence status may then be shared with other applications and other modules on the mobile device 10 or on remote devices over network 200.

Referring again to 1102, the presence status monitor 19 processes the physiological measurements 9 and may generate physiological values 8 from the physiological measurements 9. The physiological values 8 may comprise statistical values such as an average, a moving average, a standard deviation, etc. The physiological values 8 may comprise comparative values which are determined by comparing the instantaneous measurement or a moving average of a measurement with an historic value of the same measurement. For example, the presence status monitor 19 may compare the current heart rate of a user with the user's mean heart rate and standard deviation over the past month. If the user's heart rate differs significantly from the historical statistical values, the presence status monitor 19 may classify the user's instantaneous heart rate as abnormally high or abnormally low. For example, if the user's heart rate is above two standard deviations from the historical mean, the presence status monitor 19 may determine that the user's instantaneous heart rate is abnormally high.

At 1104, the presence status monitor 19 determines the physiological presence status of the user based on the processed physiological data. For example, if the presence status monitor 19 determines that the user's heart rate is abnormally high, the presence status monitor 19 may assign the user a presence of "busy" or "stressed out". As described above, the physiological presence status may be assigned based on the group with which the physiological presence status will be shared. For example, the presence status monitor 19 may assign a presence of "busy" which may be shared with colleagues and a presence of "stressed out" to be shared with friends.

The presence status monitor 19 may also combine various aspects of processed data to construct a physiological presence status. For example, a physiological sensor 34 comprising an EEG sensor, a thermometer, and a heart rate monitor, the presence status monitor 19 may determine whether any one or all of these signals are out of a normal range. The presence status monitor 19 may assign a presence status based on one or more of these signals. The presence status monitor 19 may be operable to assign a presence status based on a particular combination of signals being out of range.

For example, if the presence status monitor 19 determines that the user's heart rate is abnormally high, the user's temperature is normal, and the user's EEG signal shows that the user is actively concentrating but not using motor neurons, the presence status monitor 19 may determine that the user is under stress and assign a "stressed out" physiological presence status for friends and a "busy" physiological presence status for colleagues. However, if the presence status monitor 19 determines that the user has an abnormally high heart rate, an abnormally high temperature and the EEG signal is showing strong activity by the brain's motor neurons, the presence status monitor 19 may determine that the user is exercising and not necessarily stressed out. In this case, the presence status monitor 19 may assign a "busy" physiological presence status for colleagues but a "working out" physiological presence status for friends.

The presence status monitor 19 may also involve measurements from other sensors outside of the physiological sensor 34 in the presence status computation. For example, the presence status monitor 19 may use measurements from a GPS receiver 321, a microphone 320, and a force sensor 370 (see FIG. 18) to determine whether the user is performing certain activities. For example, while a user is running, the force sensor 370 may experience periodic impacts consistent with the user's stride and the GPS receiver 321 may experience a running velocity.

Referring to the example above, if the presence status monitor 19 determines that the user's heart rate is abnormally high, the user's temperature is abnormally high and the EEG signal is consistent with heavy activity of motor neurons, the presence status monitor 19 may also invoke GPS receiver 321 measurements and force sensor 370 measurements to determine whether the motion of the mobile device 10 is consistent with an exercise activity. If the movement of the mobile device 10 is consistent with running, for example, the presence status monitor 19 may conclude with a higher confidence that the user is exercising. The presence status monitor 19 may be operable to provide a confidence level for presence settings. The presence status monitor 19 may also save the confidence level in a presence status database.

Once the physiological presence status has been determined, it may be stored in a presence status database, which may be shared by other applications on the mobile device 10. The presence status monitor 19 may also be operable to share the presence status stored in the database with other devices. For example, the presence status monitor 19 may be operable to share the most recent presence status and physiological presence status stored in the presence status database with a device with which the mobile device 10 is in communication and has permissions to share the physiological presence status. This sharing enables a user on a remote device to view the physiological presence status of the user of the mobile device 10. The presence status monitor 19 may be operable to share the confidence of the presence status with devices with which the mobile device 10 is communicating.

A presence status monitor 19 on the remote device may also provide the presence status to various applications operating on the remote device. For example, the remote device may provide the presence status to an instant messaging application 6 on the remote device. The instant messaging application 6 may be operable to perform several actions including providing an indication of the presence status to the user of the remote device, modifying the motif of the instant message display, adjusting the audio track on the remote device based on the presence status etc. For example, if the user's presence status on the mobile device 10 is calm and relaxed, the remote device may play calming and relaxing music as well as a calm visual motif in the background of the instant messaging screen. Conversely, if the user's presence status on the mobile device 10 is enraged, the remote device may play intense music and/or provide an intense visual motif.

Figures 12, 13:
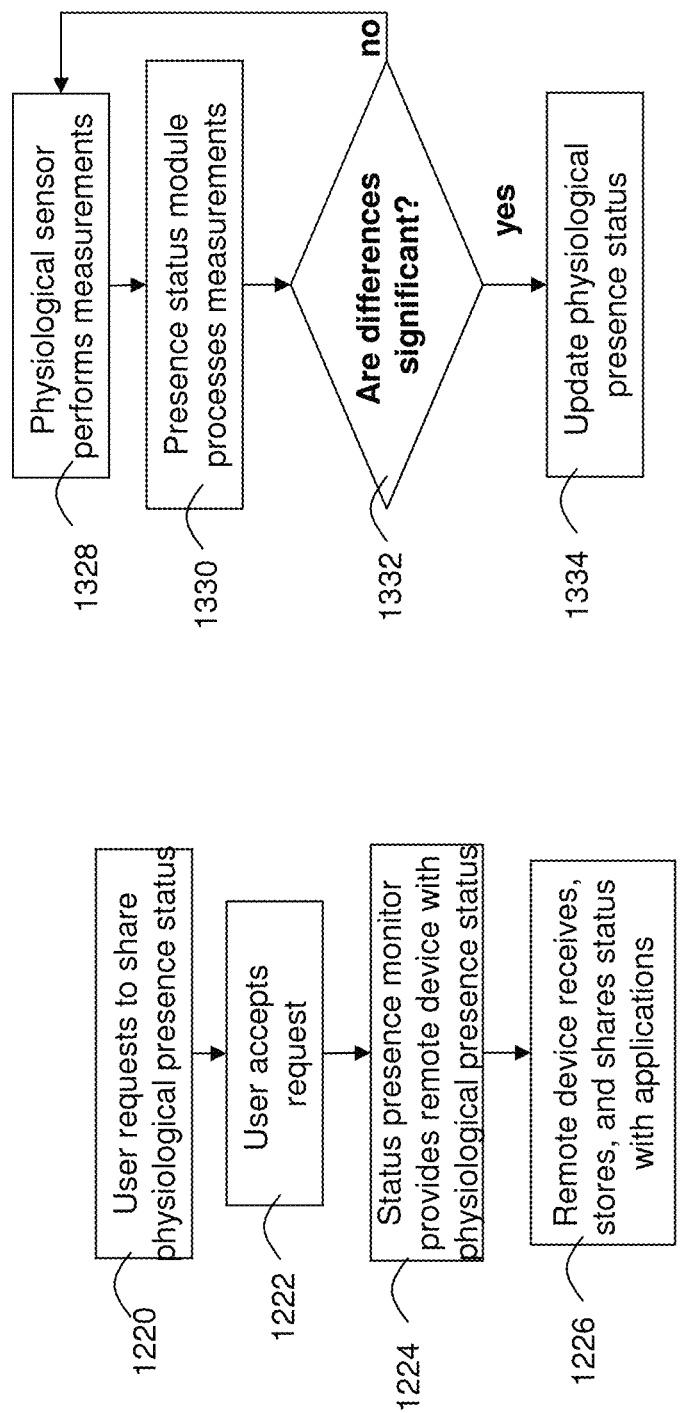
FIG. 12 is an process flow diagram of an example process for requesting to share physiological presence statuses between two devices over a network.
FIG. 13 is an process flow diagram of an example process for determining whether to update the physiological presence status.

Turning now to FIG. 12, an example set of computer executable instructions is provided, which may be executed for determining whether to share physiological presence status with a remote device. At 1220, the user of a remote device requests to share physiological presence status with the user of the mobile device 10. At 1222, the user of the mobile device 10 accepts the request to share physiological presence status. If the user of the mobile device 10 had declined the request, the presence status monitor 19 may be operable to refuse to send physiological presence status to the remote device and decline future requests. At 1224, the presence status monitor 19 provides a presence status monitor 19 of the remote device with the most recent physiological presence status. The presence status monitor 19 of the remote device may reciprocate, if granted permission, and provide the presence status monitor 19 of mobile device 10 with the physiological presence status of the user of the remote device.

At 1226, the presence status monitor 19 of the remote device shares the physiological presence status of the user of the mobile device 10 with applications and modules on the remote device. Similarly, if the presence status monitor 19 of the mobile device 10 receives the physiological status of the remote device, the presence status monitor 19 may be operable to store that physiological presence status, for example, in a presence status database, and share the physiological presence status with other applications and modules on the mobile device 10. Applications on the remote device may adjust their motif to correspond with the physiological presence status of the user of the mobile device 10.

Referring now to FIG. 13, an example set of computer executable instructions is provided that may be executed for determining whether to update the user's physiological presence status in the presence status database. Similar to FIG. 6, at 1328, the physiological sensor 34 acquires physiological measurements 9. At 1330, the presence status monitor 19 processes these physiological measurements 9 to obtain one or more physiological values 8. At 1332, the presence status monitor 19 determines whether the physiological values 8 generated at 1330 are significantly different to the physiological values generated to arrive at the current physiological presence status. If the physiological values generated at 1330 are significantly different than those used to generate the current physiological presence status, the physiological presence status is updated, as is shown at 1334. If, on the other hand, the physiological values generated at 1330 are not significantly different from those used to generate the current physiological presence status, the physiological presence status may not be updated, in which case the physiological sensor 34 may continue to monitor the user of the mobile device 10. The physiological values 8 generated at 1330 may also be compared to a moving average of previous physiological values 8, for example, to determine whether there is an abrupt change in the physiological values 8 generated at 1330. If the change in physiological values generated at 1330 is abrupt but the trend continues, the physiological presence status may also be updated.

Figure 14:
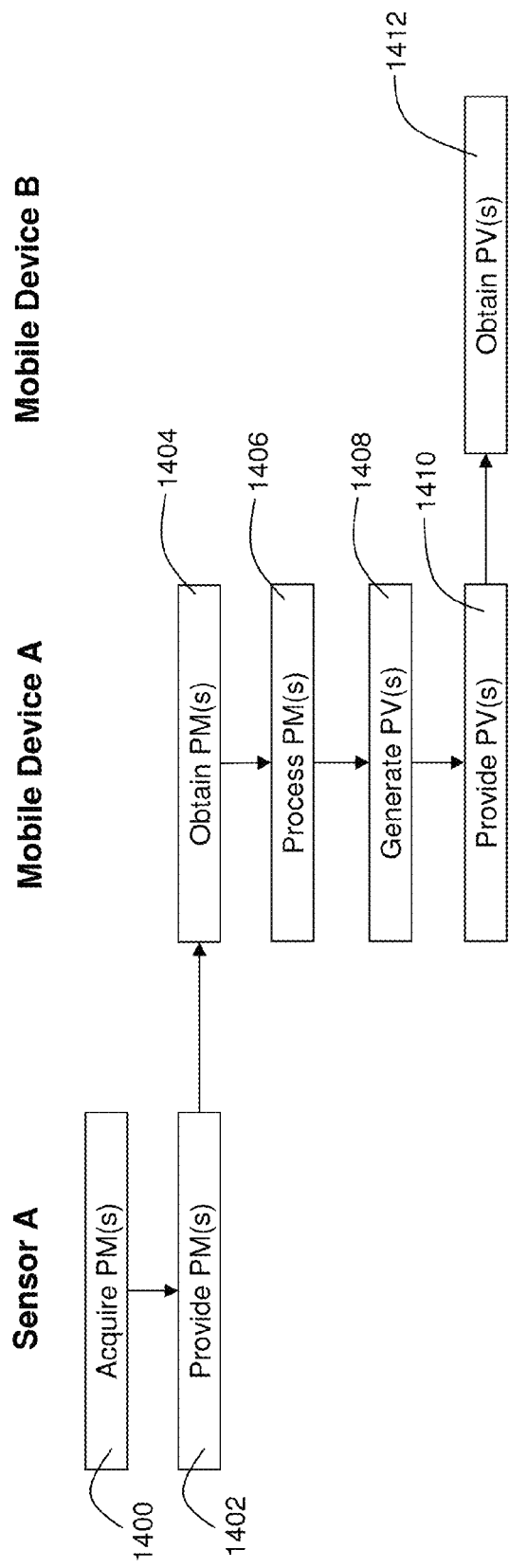
FIG. 14 is an process flow diagram of an example process of a first mobile device providing physiological presence status to a second mobile device.

Referring to FIG. 14, an example of a set of computer executable operations is shown which may be performed in having a mobile device "A" provide a presence value 8 to a mobile device "B", which is at least partly based on the user of mobile device A's status. At 1400, sensor A, which is in communication with mobile device A, acquires a physiological measurement 9. At 1402, sensor A provides the physiological measurement 9 to the physiological monitor 21 of mobile device A. The physiological monitor 21 may obtain the physiological measurement 9 through a sensor interface 7. Upon mobile device A obtaining the physiological measurement 9 at 1404, the physiological monitor 21 processes the physiological measurement 9 at 1406. Step 1406 may involve extracting key data points or statistics that may be provided to the presence status monitor 19. At 1408, the presence status monitor 21 generates a presence value 8. The presence status monitor 19 provides the presence value 8 to mobile device B at 1410, and mobile device B obtains the presence value 8 at 1412.

Figure 15:
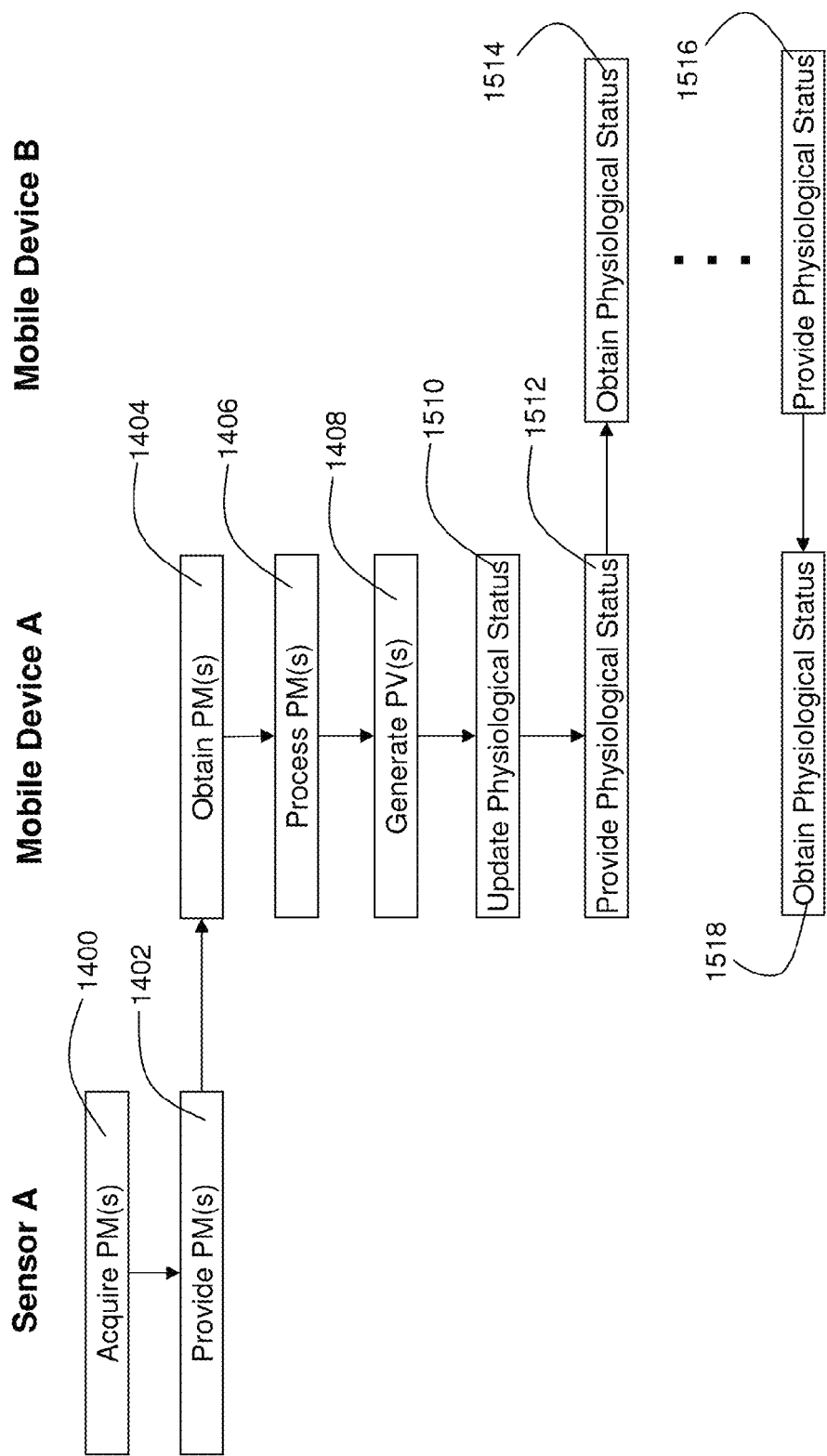
FIG. 15 is a process flow diagram of an example process for sharing physiological presence statuses between two mobile devices.

Turning now to FIG. 15, an example of a set of computer executable operations is shown which may be performed in having mobile device A share a presence status with mobile device B based solely on a physiological presence status. Operations 1400 to 1408 are performed as outlined FIG. 14, however, at 1510, the presence status monitor 19 updates the physiological presence status of the user of mobile device A. The presence status monitor 19, at 1512, provides the physiological presence status to mobile device B, which obtains the physiological presence status from mobile device A at 1514. Upon receiving physiological presence status from mobile device A, mobile device B reciprocates to provide physiological presence status to mobile device A at 1516. Mobile device A receives the physiological presence status from mobile device B at 1518.

Figure 16:
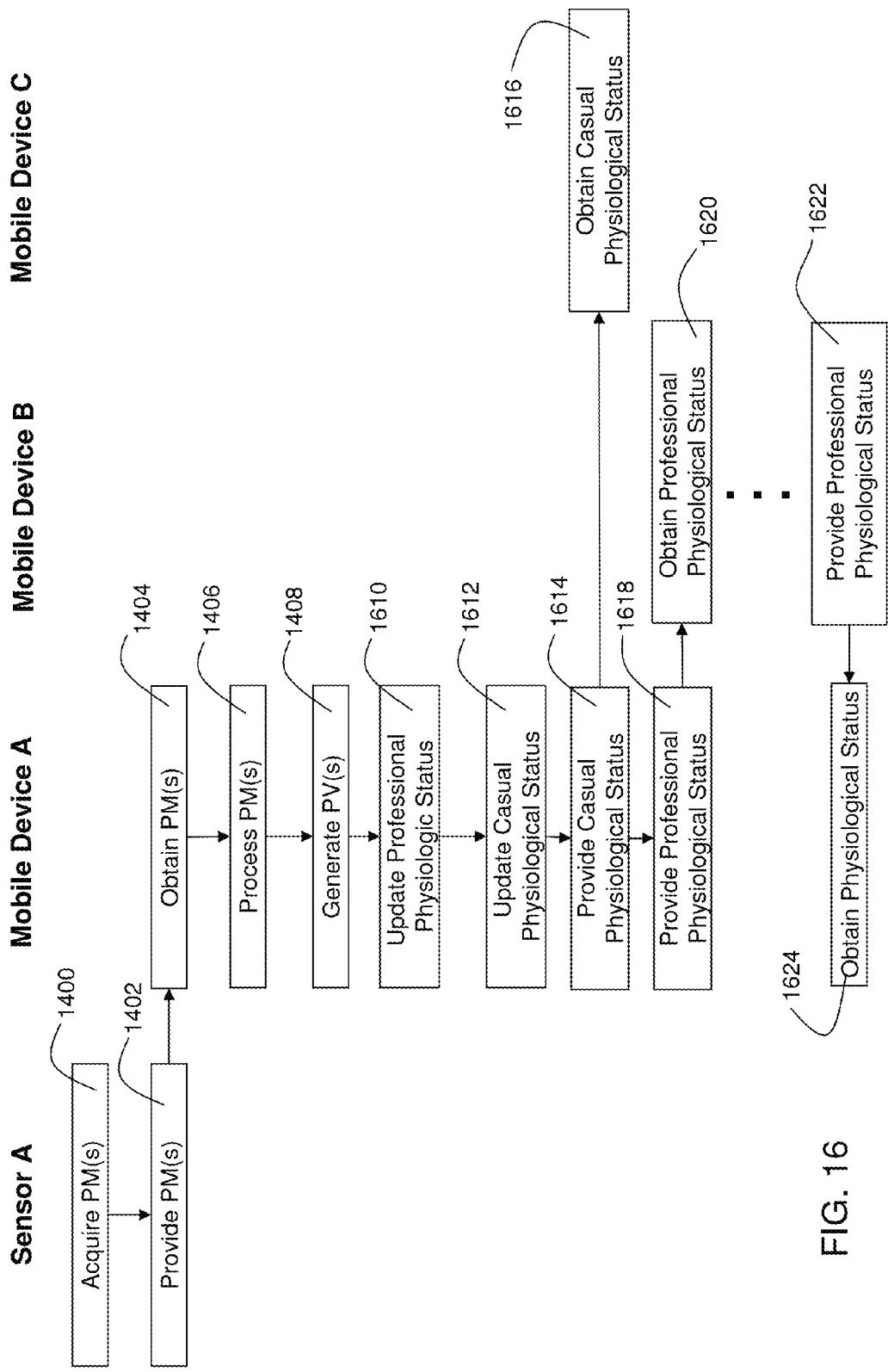
FIG. 16 is an process flow diagram of an example process for sharing professional physiological presence statuses between two devices and providing casual physiological presence status to a third device.

Turning now to FIG. 16, an example of a set of computer executable operations is shown, which may be performed in having mobile device A share a professional presence status with mobile device B based solely on a physiological presence status, and providing casual physiological presence status to mobile device C. Operations 1400 to 1408 are performed as outlined FIG. 15, however, at 1610, the presence status monitor 19 updates mobile device A's professional physiological presence status. At 1612, the presence status monitor 19 of mobile device A updates the casual physiological presence status. At 1614, mobile device A provides the casual physiological presence status to mobile device C, and mobile device C receives the casual physiological presence status from mobile device A at 1616. At 1618, mobile device A provides professional physiological presence status to mobile device B, and mobile device B obtains the professional physiological presence status from mobile device A at 1620. After receiving a physiological presence status from mobile device A, mobile device B reciprocates to provide a professional physiological presence status to mobile device A at 1622. Mobile device A receives the professional physiological presence status from mobile device B at 1624.

Figure 17:
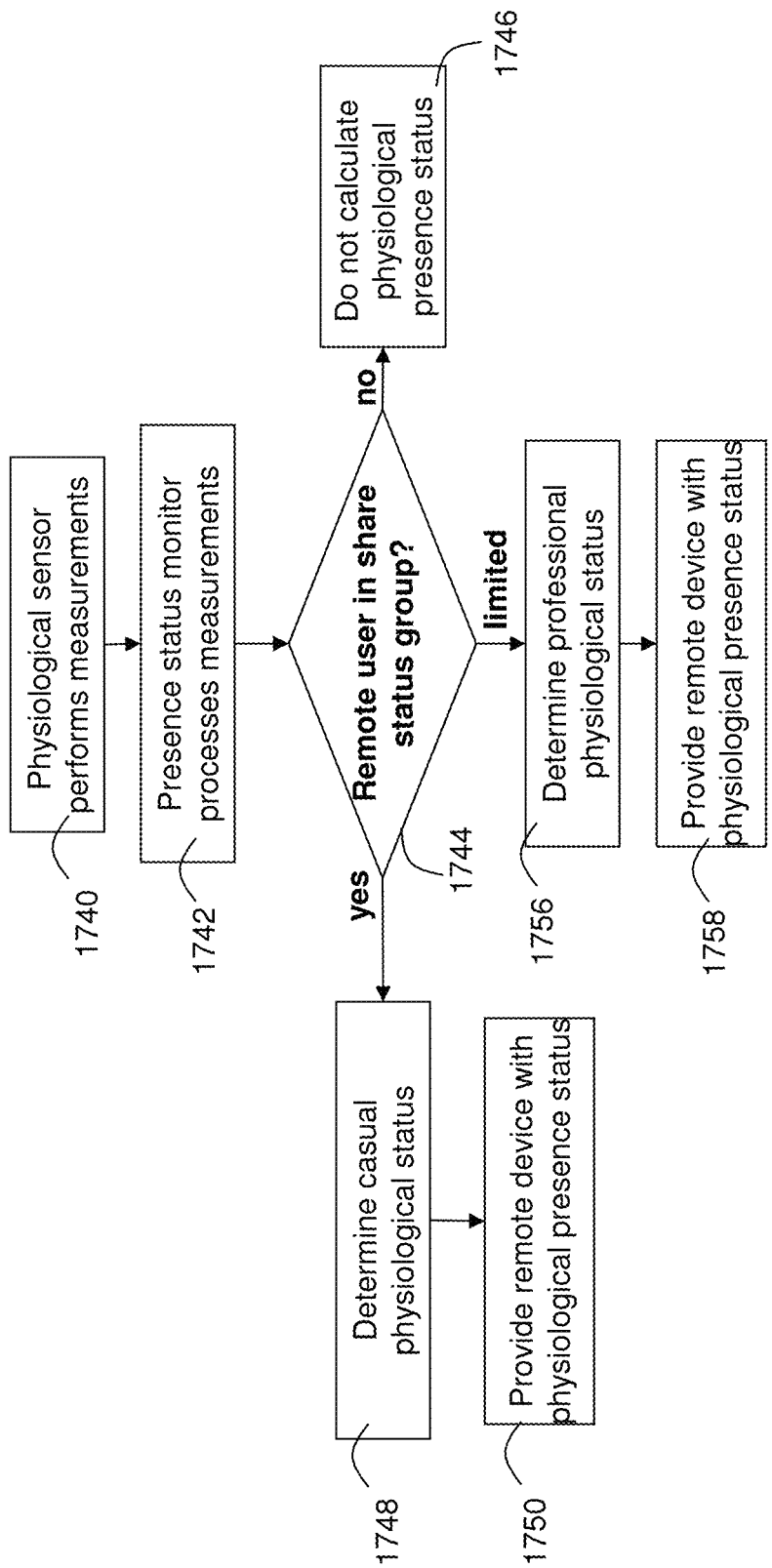
FIG. 17 is an example process flow diagram of an example process for determining which physiological presence status should be shared with a communication partner.

Referring now to FIG. 17, an example of a set of computer executable operations is shown, which may be performed by a mobile device 10 in determining which physiological presence data should be shared with remote users classified in particular groups. At 1740, similar to the operations shown in FIG. 6, the physiological sensor 34 acquires physiological measurements 9 and at 1742, the presence status monitor 19 processes these physiological measurements 9 to obtain one or more presence values 8. At 1744, the status presence monitor 19 determines in which group the remote user is classified. As indicated at 1746, if the remote user is in a group with which the status presence monitor 19 does not share the physiological presence status, the status presence monitor 19 does not calculate any physiological presence status.

Conversely, if the remote user is part of a group with which the status presence monitor 19 is authorized to share physiological presence status, the status presence monitor 19 determines the user's casual physiological status in step 1748 and shares the status at 1750. The casual physiological status may, as outlined above, comprise physiological status consistent with professional activities as well as those of casual activities. Alternatively, if the remote user is part of a group with which the status presence monitor 19 is authorized to share a limited physiological presence status, the status presence monitor 19 determines the professional physiological status of the user of the mobile device 10 at 1756. The professional physiological status may comprise more limited options than the casual physiological status. For example, the professional physiological status may comprise statuses such as "busy", "away", etc. At 1758, the status presence monitor 19 then provides the remote device with the physiological presence status that was calculated at 1756.

It can be appreciated that if a contact is in more than one group having different permission levels, a predetermined criterion can be used to select whether or not to share physiological presence status, or to what extent, for example, by choosing the more restrictive permission level.

Accordingly, there is provided a method of operating a mobile device comprising: obtaining a physiological measurement associated with a user of the mobile device; and computing a presence status using the physiological measurement.

There is also provided a method of operating a remote device communicably connectable to a mobile device, the method comprising: receiving a presence status from the mobile device, the presence status having been computed using a physiological measurement associated with a user of the mobile device.

There is also provided a computer readable storage medium comprising computer executable instructions for: obtaining a physiological measurement associated with a user of the mobile device; and computing a presence status using the physiological measurement.

There is also provided a mobile device comprising a processor, memory, and a communication module, the memory comprising computer executable instructions for: obtaining a physiological measurement associated with a user of the mobile device; and computing a presence status using the physiological measurement.

There is also provided a computer readable storage medium comprising computer executable instructions for: receiving a presence status from the mobile device, the presence status having been computed using a physiological measurement associated with a user of the mobile device.

There is also provided a remote electronic device comprising a processor, memory, and a communication module, the memory comprising computer executable instructions for: receiving a presence status from the mobile device, the presence status having been computed using a physiological measurement associated with a user of the mobile device.

Figure 18:
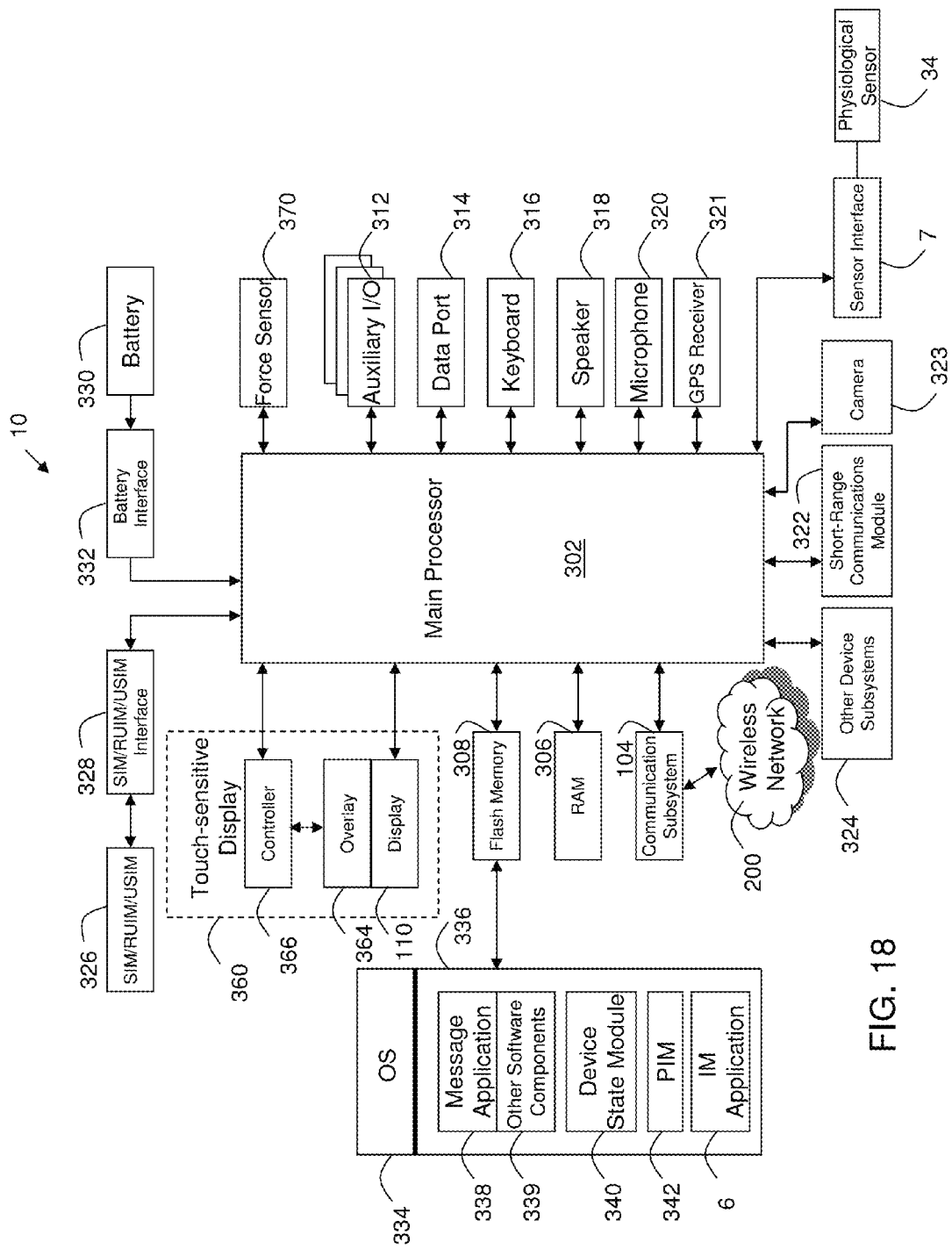
FIG. 18 is a block diagram illustrating an example of a configuration for a mobile device.

Referring to FIG. 18, to further aid in the understanding of the mobile devices 10 described above, shown therein is a block diagram of an example configuration of a mobile device 10. The mobile device 10 includes a number of components such as a main processor 302 that controls the overall operation of the mobile device 10. Communication functions, including data and voice communications, are performed through a communication subsystem 104. The communication subsystem 104 receives messages from and sends messages to a wireless network 200. In this example of the mobile device 10, the communication subsystem 104 is configured in accordance with the GSM and General Packet Radio Services (GPRS) standards, which is used worldwide. Other communication configurations that are equally applicable are the 3G and 4G networks such as Enhanced Data-rates for Global Evolution (EDGE), Universal Mobile Telecommunications System (UMTS) and High-Speed Downlink Packet Access (HSDPA), Long Term Evolution (LTE), Worldwide Interoperability for Microwave Access (Wi-Max), etc. New standards are still being defined, but it is believed that they will have similarities to the network behavior described herein, and it will also be understood by persons skilled in the art that the examples described herein are intended to use any other suitable standards that are developed in the future. The wireless link connecting the communication subsystem 104 with the wireless network 200 represents one or more different Radio Frequency (RF) channels, operating according to defined protocols specified for GSM/GPRS communications.

The main processor 302 also interacts with additional subsystems such as a Random Access Memory (RAM) 306, a flash memory 308, a touch-sensitive display 360, an auxiliary input/output (I/O) subsystem 312, a data port 314, a keyboard 316 (physical, virtual, or both), a speaker 318, a microphone 320, a GPS receiver 321, short-range communications module 322, a camera 323, a sensor interface 7 coupled to a physiological sensor 34, and other device subsystems 324. Some of the subsystems of the mobile device 10 perform communication-related functions, whereas other subsystems may provide "resident" or on-device functions. By way of example, the display 360 and the keyboard 316 may be used for both communication-related functions, such as entering a text message for transmission over the wireless network 200, and device-resident functions such as a calculator or task list. In one example, the mobile device 10 can include a non touch-sensitive display in place of, or in addition to the touch-sensitive display 360. For example the touch-sensitive display 360 can be replaced by a display 110 that may not have touch-sensitive capabilities.

The mobile device 10 can send and receive communication signals over the wireless network 200 after required network registration or activation procedures have been completed. Network access is associated with a subscriber or user of the mobile device 10. To identify a subscriber, the mobile device 10 may use a subscriber module component or "smart card" 326, such as a SIM, a Removable User Identity Module (RUIM) and a Universal Subscriber Identity Module (USIM). In the example shown, a SIM/RUIM/USIM 326 is to be inserted into a SIM/RUIM/USIM interface 328 in order to communicate with a network.

The mobile device 10 is typically a battery-powered device and includes a battery interface 332 for receiving one or more rechargeable batteries 330. In at least some examples, the battery 330 can be a smart battery with an embedded microprocessor. The battery interface 332 is coupled to a regulator (not shown), which assists the battery 330 in providing power to the mobile device 10. Although current technology makes use of a battery, future technologies such as micro fuel cells may provide the power to the mobile device 10.

The mobile device 10 also includes an operating system 334 and software components 336 to 342, and 6. The operating system 334 and the software components 336 to 342, and 6 that are executed by the main processor 302 are typically stored in a persistent store such as the flash memory 308, which may alternatively be a read-only memory (ROM) or similar storage element (not shown). Those skilled in the art will appreciate that portions of the operating system 334 and the software components 336 to 342, and 6 such as specific device applications, or parts thereof, may be temporarily loaded into a volatile store such as the RAM 306. Other software components can also be included, as is well known to those skilled in the art.

The subset of software applications 336 that control basic device operations, including data and voice communication applications, may be installed on the mobile device 10 during its manufacture. Software applications may include a message application 338, a device state module 340, a Personal Information Manager (PIM) 342, and an IM application 6. A message application 338 can be any suitable software program that allows a user of the mobile device 10 to send and receive electronic messages, wherein messages are typically stored in the flash memory 308 of the mobile device 10. A device state module 340 provides persistence, i.e. the device state module 340 ensures that important device data is stored in persistent memory, such as the flash memory 308, so that the data is not lost when the mobile device 10 is turned off or loses power. A PIM 342 includes functionality for organizing and managing data items of interest to the user, such as, but not limited to, e-mail, contacts, calendar events, and voice mails, and may interact with the wireless network 200.

Other types of software applications or components 339 can also be installed on the mobile device 10. These software applications 339 can be pre-installed applications (i.e. other than message application 338) or third party applications, which are added after the manufacture of the mobile device 10. Examples of third party applications include games, calculators, utilities, etc.

The additional applications 339 can be loaded onto the mobile device 10 through at least one of the wireless network 200, the auxiliary I/O subsystem 312, the data port 314, the short-range communications module 322, or any other suitable device subsystem 324.

The data port 314 can be any suitable port that enables data communication between the mobile device 10 and another computing device. The data port 314 can be a serial or a parallel port. In some instances, the data port 314 can be a USB port that includes data lines for data transfer and a supply line that can provide a charging current to charge the battery 330 of the mobile device 10.

For voice communications, received signals are output to the speaker 318, and signals for transmission are generated by the microphone 320. Although voice or audio signal output is accomplished primarily through the speaker 318, the display 110 can also be used to provide additional information such as the identity of a calling party, duration of a voice call, or other voice call related information.

The touch-sensitive display 360 may be any suitable touch-sensitive display, such as a capacitive, resistive, infrared, surface acoustic wave (SAW) touch-sensitive display, strain gauge, optical imaging, dispersive signal technology, acoustic pulse recognition, and so forth, as known in the art. In the presently described example, the touch-sensitive display 360 is a capacitive touch-sensitive display which includes a capacitive touch-sensitive overlay 364. The overlay 364 may be an assembly of multiple layers in a stack which may include, for example, a substrate, a ground shield layer, a barrier layer, one or more capacitive touch sensor layers separated by a substrate or other barrier, and a cover. The capacitive touch sensor layers may be any suitable material, such as patterned indium tin oxide (ITO).

The display 110 of the touch-sensitive display 360 may include a display area in which information may be displayed, and a non-display area extending around the periphery of the display area. Information is not displayed in the non-display area, which is utilized to accommodate, for example, electronic traces or electrical connections, adhesives or other sealants, and/or protective coatings around the edges of the display area.

In some examples, an optional force sensor 370 or force sensors is disposed in any suitable location, for example, between the touch-sensitive display 360 and a back of the mobile device 10 to detect a force imparted by a touch on the touch-sensitive display 360. The force sensor 370 may be a force-sensitive resistor, strain gauge, piezoelectric or piezoresistive device, pressure sensor, or other suitable device. Force as utilized throughout the specification refers to force measurements, estimates, and/or calculations, such as pressure, deformation, stress, strain, force density, force-area relationships, thrust, torque, and other effects that include force or related quantities.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device 10, or accessible or connectable thereto. Any application or module herein described may be implemented using computer readable/executable instructions that may be stored or otherwise held by such computer readable media.

It will be appreciated that the example embodiments and corresponding diagrams used herein are for illustrative purposes only. Different configurations and terminology can be used without departing from the principles expressed herein. For example, components and modules can be added, deleted, modified, or arranged with differing connections without departing from these principles.

The steps or operations in the flow charts and diagrams described herein are just for example. There may be many variations to these steps or operations without departing from the spirit of the invention or inventions. For instance, the steps may be performed in a differing order, or steps may be added, deleted, or modified.

Although the above principles have been described with reference to certain specific example embodiments, various modifications thereof will be apparent to those skilled in the art as outlined in the appended claims.

The invention claimed is:

1. A method of operating a mobile device comprising:
   obtaining a physiological measurement associated with a user of the mobile device;
   determining a first presence status indicative of a first emotional state using the physiological measurement;
   determining a second presence status indicative of a second emotional state using the same physiological measurement;
   incorporating the first presence status and the second presence status into one of a plurality of presence states used by a messaging application;
   displaying at least one of the first and second presence states with the presence status indicative of the emotional state in a user interface for the messaging application on the mobile device; and
   providing the first presence status to a first group of contacts to have the first group of contacts display the presence state with the first presence status indicative of the first emotional state and providing the second presence status to a second group of contacts to have the second group of contacts display the presence state with the second presence status indicative of the second emotional state.

2. The method of claim 1, the first group of contacts being associated with personal contacts, and the second group of contacts being associated with professional contacts.

3. The method of claim 1, further comprising displaying a presence status indicator on the mobile device.

4. The method of claim 1, the physiological measurement being obtained from a physiological sensor coupled to the mobile device.

5. The method of claim 1, the physiological measurement being obtained from a physiological sensor in an external device coupled to the mobile device.

6. The method of claim 1, further comprising computing a presence value using the physiological measurement, and using the presence value to generate the presence status.

7. The method of claim 1, further comprising receiving a presence status from a remote device and displaying the presence status from the remote device on the mobile device, the presence status from the remote device being associated with a physiological measurement for a user of the remote device.

8. The method of claim 1, wherein the first presence status is selected from less than a range of emotional states that can be provided using the second presence status.

9. A method of operating a remote device communicably connectable to a mobile device, the method comprising:
   receiving a first presence status from the mobile device indicative of a first emotional state of a user of the mobile device and generated for a first group of contacts of the mobile device, the first presence status having been generated using a physiological measurement associated with the user of the mobile device and incorporated into one of a plurality of presence states used by a messaging application, the first presence status and first emotional state being different than a second presence status and second emotional state determined using the same physiological measurement and having been sent to a second group of contacts of the mobile device; and
   displaying the presence state with the first presence status indicative of the first emotional state on the remote device in a user interface for the messaging application.

10. The method of claim 9 further comprising initiating a media item associated with the received presence status.

11. The method of claim 9, the first group of contacts being associated with personal contacts, and the second group of contacts being associated with professional contacts.

12. The method of claim 9, further comprising displaying a presence status indicator on the mobile device.

13. The method of claim 9, the presence status having been generated using a presence value computed by the mobile device.

14. The method of claim 9, further comprising computing another presence status indicative of an emotional state using a physiological measurement associated with a user of the remote device, and sending the other presence status from the remote device to the mobile device.

15. A non-transitory computer readable storage medium comprising computer executable instructions for:
   obtaining a physiological measurement associated with a user of the mobile device;
   determining a first presence status indicative of a first emotional state using the physiological measurement;
   determining a second presence status indicative of a second emotional state using the same physiological measurement;
   incorporating the first presence status and the second presence status into one of a plurality of presence states used by a messaging application;
   displaying at least one of the first and second presence states with the presence status indicative of the emotional state in a user interface for the messaging application on the mobile device; and
   providing the first presence status to a first group of contacts to have the first group of contacts display the presence state with the first presence status indicative of the first emotional state and providing the second presence status to a second group of contacts to have the second group of contacts display the presence state with the second presence status indicative of the second emotional state.

16. A mobile device comprising a processor, memory, and a communication module, the memory comprising computer executable instructions for:
   obtaining a physiological measurement associated with a user of the mobile device;
   determining a first presence status indicative of a first emotional state using the physiological measurement;
   determining a second presence status indicative of a second emotional state using the same physiological measurement;
   incorporating the first presence status and the second presence status into one of a plurality of presence states used by a messaging application;
   displaying at least one of the first and second presence states with the presence status indicative of the emotional state in a user interface for the messaging application on the mobile device; and
   providing the first presence status to a first group of contacts to have the first group of contacts display the presence state with the first presence status indicative of the first emotional state and providing the second presence status to a second group of contacts to have the second group of contacts display the presence state with the second presence status indicative of the second emotional state.

17. A non-transitory computer readable storage medium comprising computer executable instructions for:
   receiving a first presence status from the mobile device indicative of a first emotional state of a user of the mobile device and generated for a first group of contacts of the mobile device, the first presence status having been generated using a physiological measurement associated with the user of the mobile device and incorporated into one of a plurality of presence states used by a messaging application, the first presence status and first emotional state being different than a second presence status and second emotional state determined using the same physiological measurement and having been sent to a second group of contacts of the mobile device; and
   displaying the presence state with the first presence status indicative of the first emotional state on the remote device in a user interface for the messaging application.

18. A remote electronic device comprising a processor, memory, and a communication module, the memory comprising computer executable instructions for:
   receiving a first presence status from the mobile device indicative of a first emotional state of a user of the mobile device and generated for a first group of contacts of the mobile device, the first presence status having been generated using a physiological measurement associated with the user of the mobile device and incorporated into one of a plurality of presence states used by a messaging application, the first presence status and first emotional state being different than a second presence status and second emotional state determined using the same physiological measurement and having been sent to a second group of contacts of the mobile device; and
   displaying the presence state with the first presence status indicative of the first emotional state on the remote device in a user interface for the messaging application.

* * * * *